(12) United States Patent
Ganti

(10) Patent No.: US 8,157,757 B2
(45) Date of Patent: Apr. 17, 2012

(54) SPECIAL BED TO SELF INDUCE BODY TRACTION

(76) Inventor: Sastry K Ganti, Buffalo Grove, IL (US)

( * ) Notice: Subject to any disclaimer, the term of this patent is extended or adjusted under 35 U.S.C. 154(b) by 0 days.

(21) Appl. No.: 12/924,366

(22) Filed: Sep. 27, 2010

(65) Prior Publication Data

US 2011/0214236 A1    Sep. 8, 2011

Related U.S. Application Data

(60) Provisional application No. 61/339,697, filed on Mar. 8, 2010.

(51) Int. Cl.
*A61F 5/00*    (2006.01)
*A47B 7/00*    (2006.01)
(52) U.S. Cl. .................. 602/32; 602/33; 5/621
(58) Field of Classification Search .......... 602/32, 602/33, 34, 35, 36, 37, 38; 128/845, 846, 128/857; 5/621–624, 632, 643, 650, 647, 660, 509.1

See application file for complete search history.

(56) References Cited

U.S. PATENT DOCUMENTS

| | | | |
|---|---|---|---|
| 2,822,805 A | 2/1958 | Hill | |
| 3,353,532 A | 11/1967 | Ellis | |
| 3,669,102 A | 6/1972 | Harris | |
| 4,282,868 A | 8/1981 | Riggs | |
| 5,052,378 A | 10/1991 | Chitwood | |
| 5,713,841 A * | 2/1998 | Graham | 602/32 |
| 6,966,321 B2 * | 11/2005 | Hess | 128/870 |

* cited by examiner

*Primary Examiner* — Patricia Bianco
*Assistant Examiner* — Ophelia Hawthorne

(57) ABSTRACT

A special bed and apparatus, having a fixed section and a movable section, supports a person lying face up, and allows self to restrain two regions of self's body, one on the fixed section and another on the movable section, and further allows the person to self induce traction force between the restrained regions.

1 Claim, 17 Drawing Sheets

SPECIAL BED TO SELF INDUCE BODY TRACTION

CROSS-REFERENCE TO RELATED APPLICATION

Figure 1:
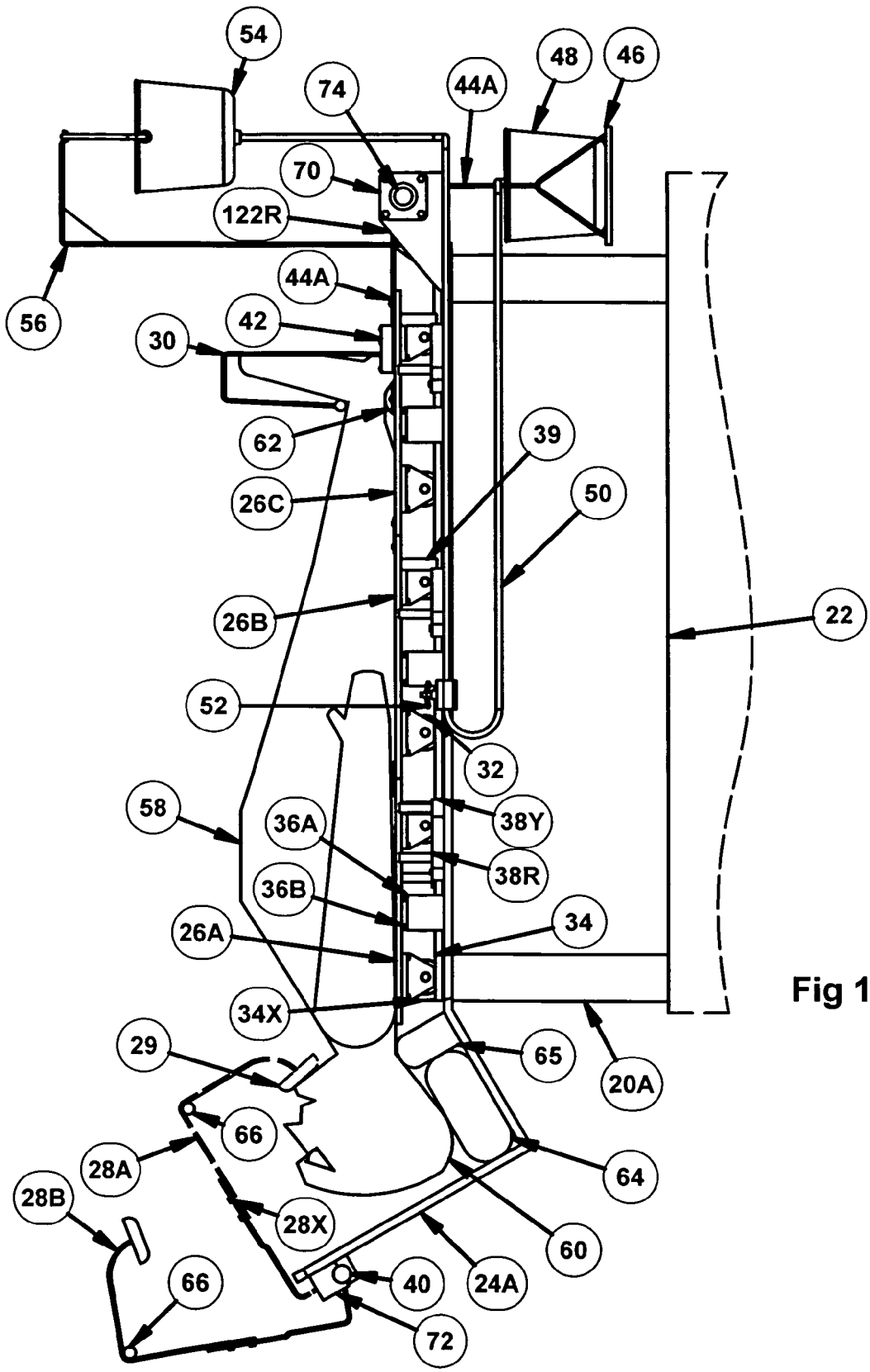

This application claims the benefit of provisional patent application, serial number U.S. 61/339,697, filed Mar. 8, 2010, confirmation number 7426.

FEDERALLY SPONSORED RESEARCH

Not applicable

SEQUENCE LISTING OR PROGRAM

Not Applicable

BACKGROUND OF THE INVENTION

Field of Invention

This invention relates to special beds, attached apparatuses and methods for self inducing and self managing body traction force to one or more of body joints, with the person lying face up on the bed.

BACKGROUND OF THE INVENTION, PRIOR ART

It is a fact of the prior art that, even health conscious individuals do not pay much attention to the wellness of their internal thin body parts, namely the compressive, elastic materials housed between bones at their joints. These are disks and cartilages at vertebrae, ankles, knees, hips etc. Even though these take much constant abuse throughout life, no routine attention giving procedure seems to exist starting early in life for these thin body parts so that they will grow healthy and stay so.

Attention to these thin body parts is unconsciously delayed till later years of life, by when their gradual degradation manifests into painful problems. Pinched nerves, ruptured disks, bone grinding on bone, onset of arthritis and such, are a few of the problems faced, when it is late for one to do anything by self. Professional diagnosis, procedures and treatment are then needed, inclusive often of strong medication.

For much of life, significant attention is directed to diet, exercise, health and strength of the more common and popular body items, such as muscles, bones, skin, blood vessels, etc. Resistance and cardio vascular exercises, breathing, relaxation and meditation techniques, etc., get much of the focus. A whole host of apparatuses and procedures are available for the stated.

Even the ancient and modern relaxation techniques, though helping many body parts and body functions, do not relieve these thin body parts of their stress, unless the body is completely lying down in a sleeping posture.

The thin body parts embedded at the joint areas of bones are under constant compressive forces due body activity or plain stacked weight of parts they support. These forces do put some squeeze on any blood vessels and nerves passing through them, hampering the nutrient and blood flow crossing into the interior, bringing the adjacent bones a bit too close to flow of body information. In addition to gradually becoming materially degraded and less flexible, they are subjected to thinning and rupturing. They get relief only when the person completely lies down in a sleeping posture. Only then all weight and forces on them are removed. A health conscious individual is seldom aware of methods of relieving stress and trauma to these thin body parts, let alone knowing methods to make them healthier at an earlier stage of life. Seldom any health center or home has any equipment or any physical routine for the maintenance of these thin body parts.

In certain tribes of the less developed world, female children are subjected to placement of permanent metal rings, stacked as a column around the neck at an early age. Though this is a form of inducing localized traction force, it is to elongate their necks permanently and it is considered a process of beautification of the girl. Far from being a health improving procedure, such drastic procedure of inducing a large separating force between the cervical vertebrae, deforms the bones forming the shoulder and the rib cage. It leaves the body structure above shoulders perpetually unstable to handle any tilt.

Since no routine in prior art is available for joint health, when a person reaches about 40+ years of age, joint pains, fluids in joints, damaged disks, pinching on nerves,—such pain giving problems begin to show up. The intensity of discomfort increases with age. Relief from such problems always seems to involve the need of doctors, chiropractors, nurses, rehabilitation centers, medical centers. Some self administered fixture apparatuses, though inadequate, are available. Rarely the individual has ideas or options to do routinely by self, something earlier or later in life in conjunction with the more popular exercise and diet routines that would strengthen these thin body parts, and subsequently delay substantially the onset of the problems stated.

Further, counting ~26 thin body parts, stacked from feet to the base of one's head (23 disks at the vertebrae, say +1 ankle, +1 knee and +1 hip), if each of these parts was to be thicker by just 0.03", the person would gain ~¾" additional height due to healthy joints alone. Prior art has not looked at joint health this way. It is probable that since nothing is done consciously and frequently to reverse the stress on the thin body parts at any stage of life, a person's healthy height may be self compromised.

Summarizing the deficiencies in the prior art:
  (a) Conscious healthcare of thin body parts and joints is neglected,
  (b) No suitable apparatuses or methods for early life heath care of body's joints and thin body parts are available,
  (c) Expensive professional healthcare is often the only recourse for joint problems,
  (d) Onset of ill health to materials at joints arrives much sooner than it should,
  (e) Routine self health procedures for body's joints, conveniently at home or heath care centers, along with aerobic and/or resistance exercises, is not available,
  (f) An individual may be sacrificing body height by neglecting body's joints' health.

BACKGROUND OF THE INVENTION, OBJECTS AND ADVANTAGES

The apparatuses and the methods of the present invention describe specialized beds with simple attachments, for an individual to rest in a sleeping posture, face up, and subject self's body to carefully self controlled traction force, routinely. Traction may be applied after normally tiring activities of daily work, weight training, calisthenics, or aerobics, etc. or, at any other preferred time, for any desired duration.

The bed and attached apparatuses of the invention make up five defining sections:

(1) a fixed bed frame section to maintain non movable from any horizontal movement one desired part of the person's body, say its head. This section has provision where the head is supported and restrained from any horizontal movement. The head is held at a small inclined position, face looking up and to the rear. This hyperextension aids in resisting the induced traction force, with no discomfort.

(Though it is the head, described predominantly as restrained body part from any horizontal movement, any other body part or combination of parts at one end of the body can be restrained, if the fixed frame is designed so to accommodate.)

(2) an apparatus comprising of a chin restraining mechanism with chin obstruction pad or bar, and a restraining pad near the rear lobe of the head near the occipital skull bone of the person, both attached to the fixed bed frame section. This assures that the head stays in a fixed position from any horizontal movement when under traction. The chin restraint in conjunction with the head lobe restraint, and hyperextension will add maximum comfort and effectiveness in resisting the induced traction force.

(3) a horizontally movable platform section, supported by the fixed bed frame section. It is free to move horizontally on wheels in tracks with minimum friction, so that most of the horizontal pull force generated transmits as induced traction force. This section is made up of two or more substantially similar modules. The remainder of the body (neck to feet) can be supported by the platforms of these modules. One module can be connected to its adjacent one to make both behave as one unit. Any module can have its horizontal mobility arrested by temporarily latching it to the fixed bed frame section. It then becomes a part of the non movable platform section.

(4) a section comprising of feet restraining mechanisms. They are mounted on the horizontally movable platform module farthest from the head. They restrain the feet and their heels from moving horizontally relative to the moving platform on which they are mounted.

(5) an apparatus comprising the traction force generating and inducing components. Portions of it are mounted to horizontally movable platforms and portions are mounted to the non movable platforms. Traction force generated by the apparatus is ultimately transmitted to the restraints on the person's body on a movable platform. The apparatus is self operated by the person on the bed. All controls are mounted close to the person's arms.

Accordingly, the objects and advantages of invention presented here are:

(a) A person will have simple apparatuses readily available to use and simple methods by which to self induce traction force for good health, routinely, starting early in life. Just as a person routinely performs aerobics and running for cardiovascular health, resistance exercises and weightlifting for stronger muscles and bones, breathing and meditation exercises for hypertension and a multitude of other benefits, the person can go through several times a week, carefully controlled self induced traction for the health and growth of the thin body parts.

(b) The inducing of traction force can be done in the comfort of home, gymnasiums or other public places, and even when away from home traveling.

(c) There will be more freedom for the duration of the induced traction force.

(d) The inducing of traction force can be initiated at any desired time of the day.

(e) The apparatus can be inexpensively built and marketed.

(f) No expenses of the help of healthcare professionals are required.

(g) With the traction force induced routinely as part of health exercise, any development of joint problems later-in-life may be delayed by several years or eliminated altogether.

(h) The damaging pinching forces on thin body parts will not only be relieved to make the person feel good, under traction force they will be reversed to become negative, thus facilitating better blood and nutrient flow to the interior of the thin body parts.

(i) It is probable that the thin body parts will become thicker due to the health routine of induced traction force, and probably will add to the height of the individual.

(k) The added healthy tissue of the thin body parts will withstand the wear and tear at joints better, and will help individuals involved in intensely joint pounding athletic activities such as track, football, basketball, gymnastics, and the like.

SUMMARY

In accordance with the presented invention, the apparatus consists of a specialized bed with attachments, wherein an individual can set self to lie on the bed in sleeping posture, facing up, and self restrain safely one end of self's body to the horizontally non movable end of the bed, restrain the other end of self's body safely on the horizontally movable platform of the bed, and proceed to self induce in self's body required amount of traction force for desired period of time.

DRAWINGS, FIGURES

FIG. 1 Bed using weight of transferred liquid for traction, elevation view

Figure 2:
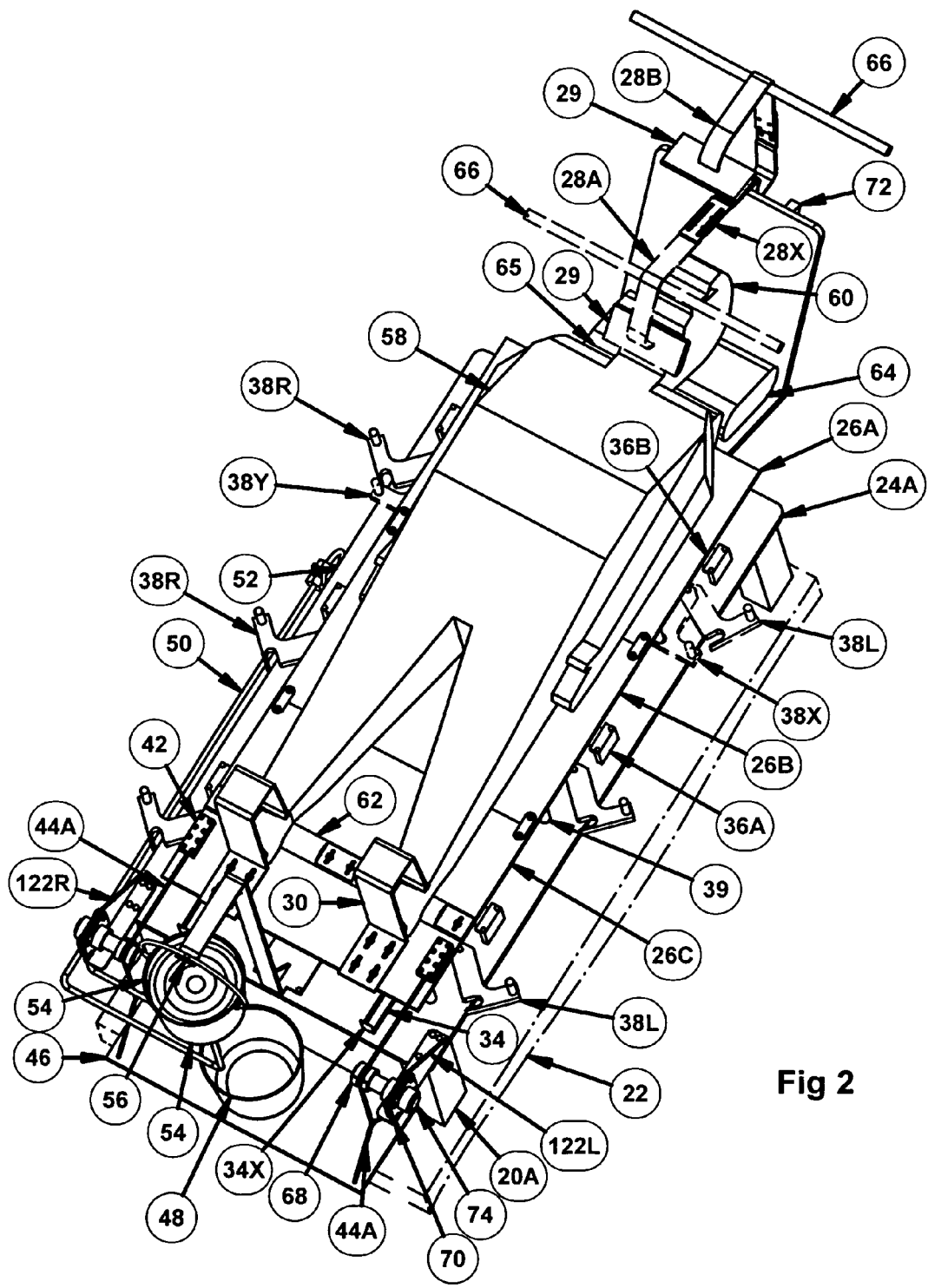

FIG. 2 Bed using weight of transferred liquid for traction, perspective view

Figure 3:
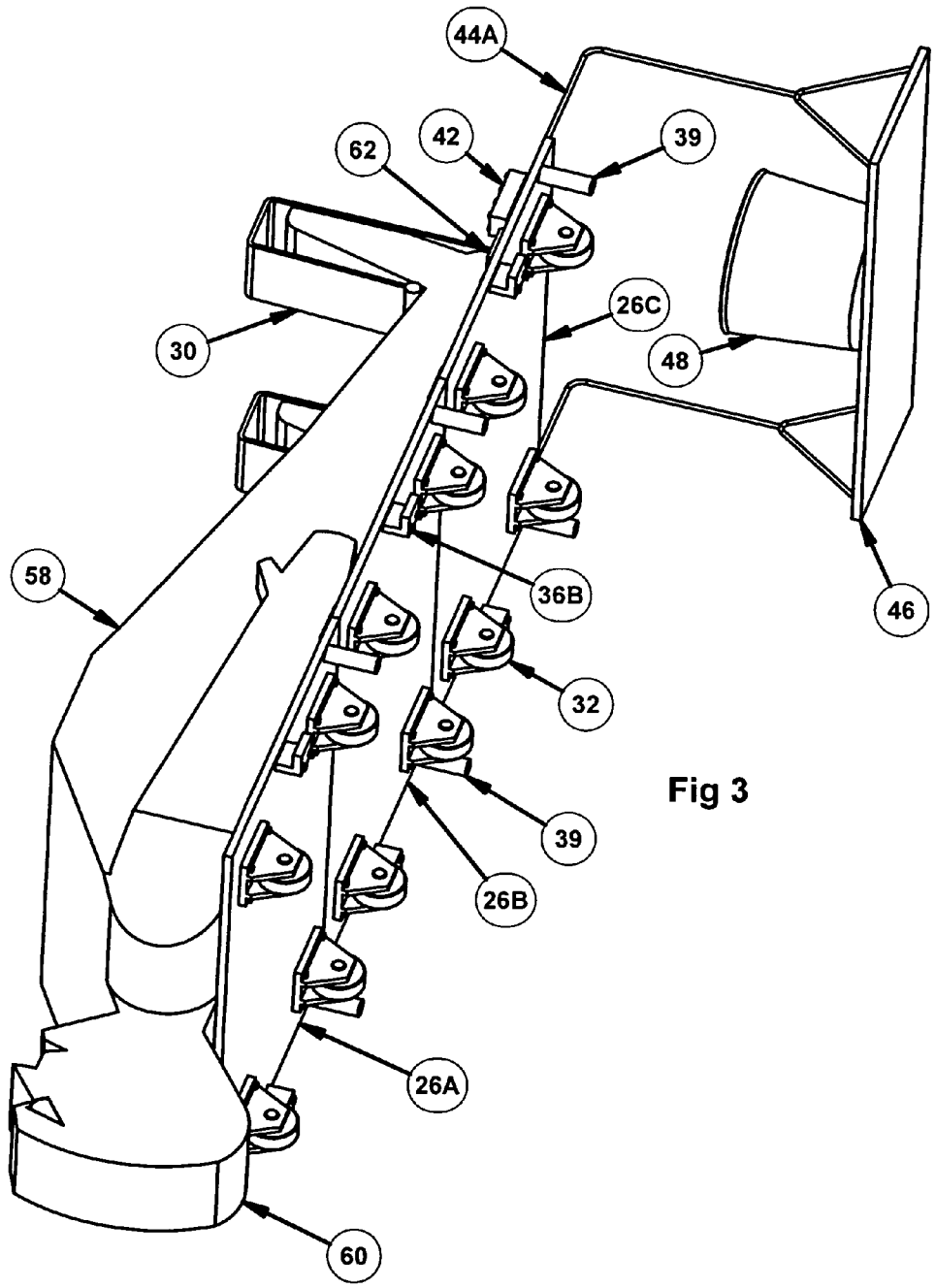

FIG. 3 Movable platforms and movable parts/weight of liquid for traction

Figure 4:
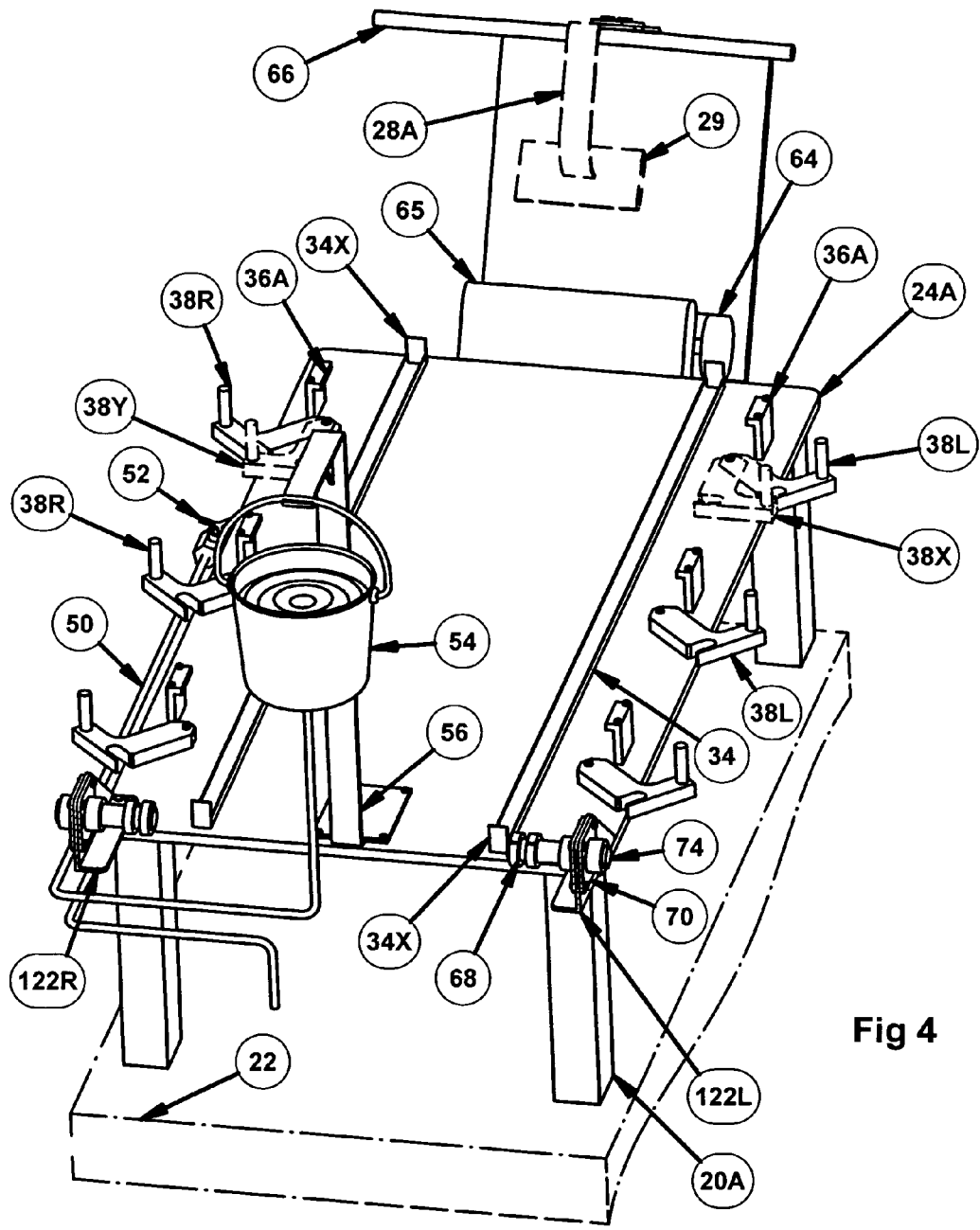

FIG. 4 Non movable platform and other parts/weight of liquid for traction

Figure 5:
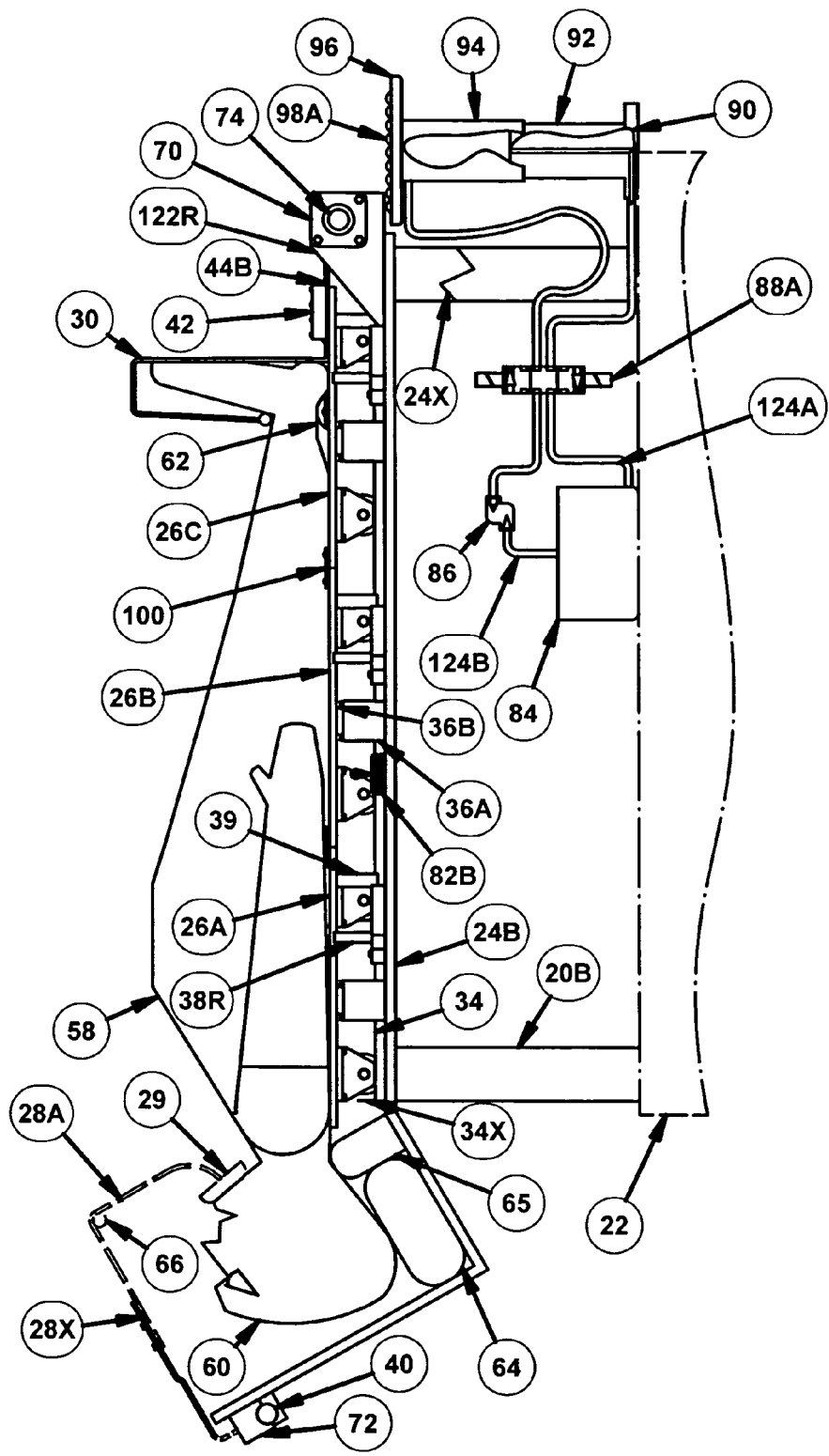

FIG. 5 Bed using weights in tray/no traction/lifted tray supporting weights

Figure 6:
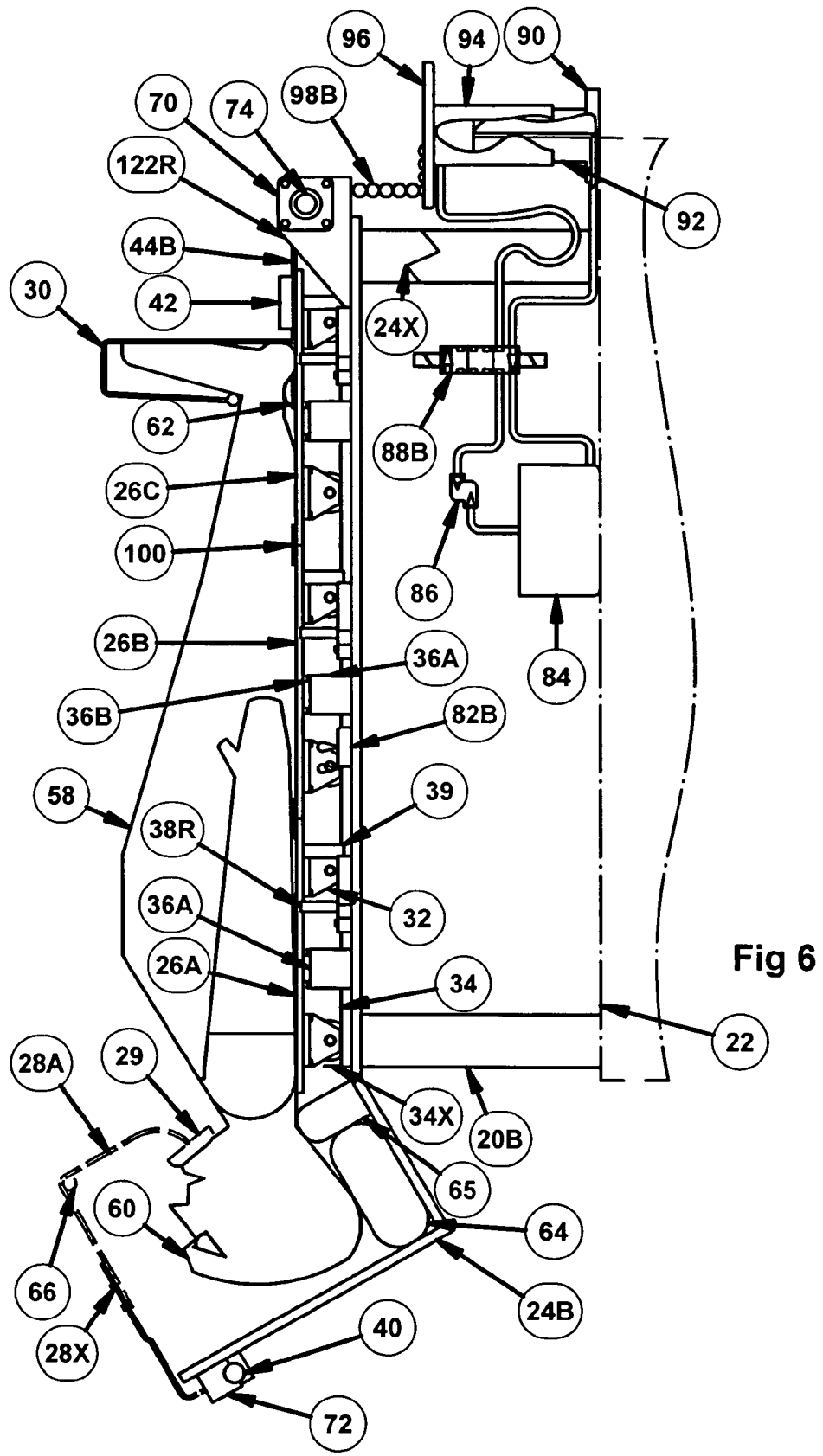

FIG. 6 Bed using weights in tray/traction induced/tray lowered

Figure 7:
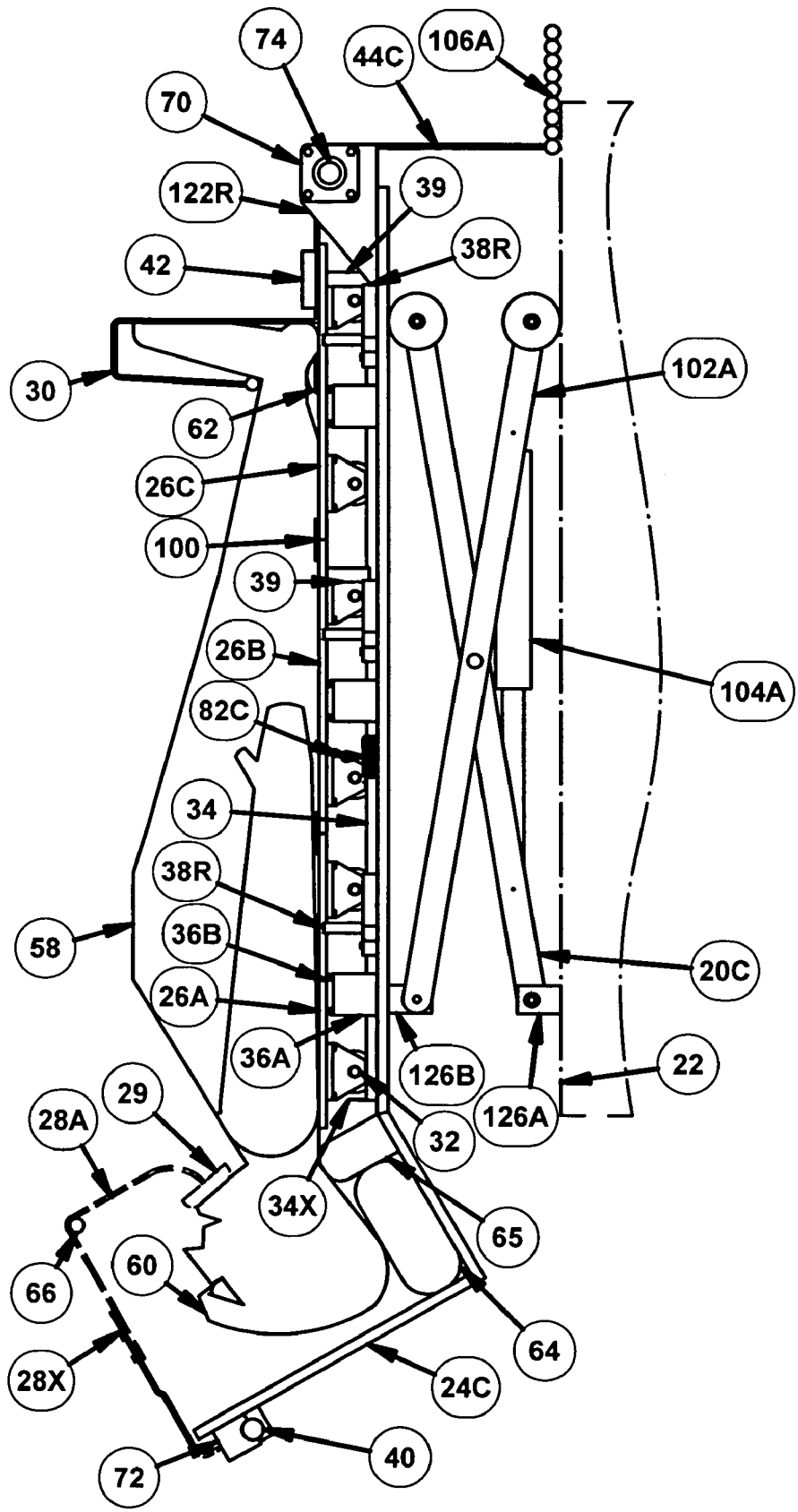

FIG. 7 Bed on bed lifting frame/bed lowered/weights supported/no traction

Figure 8:
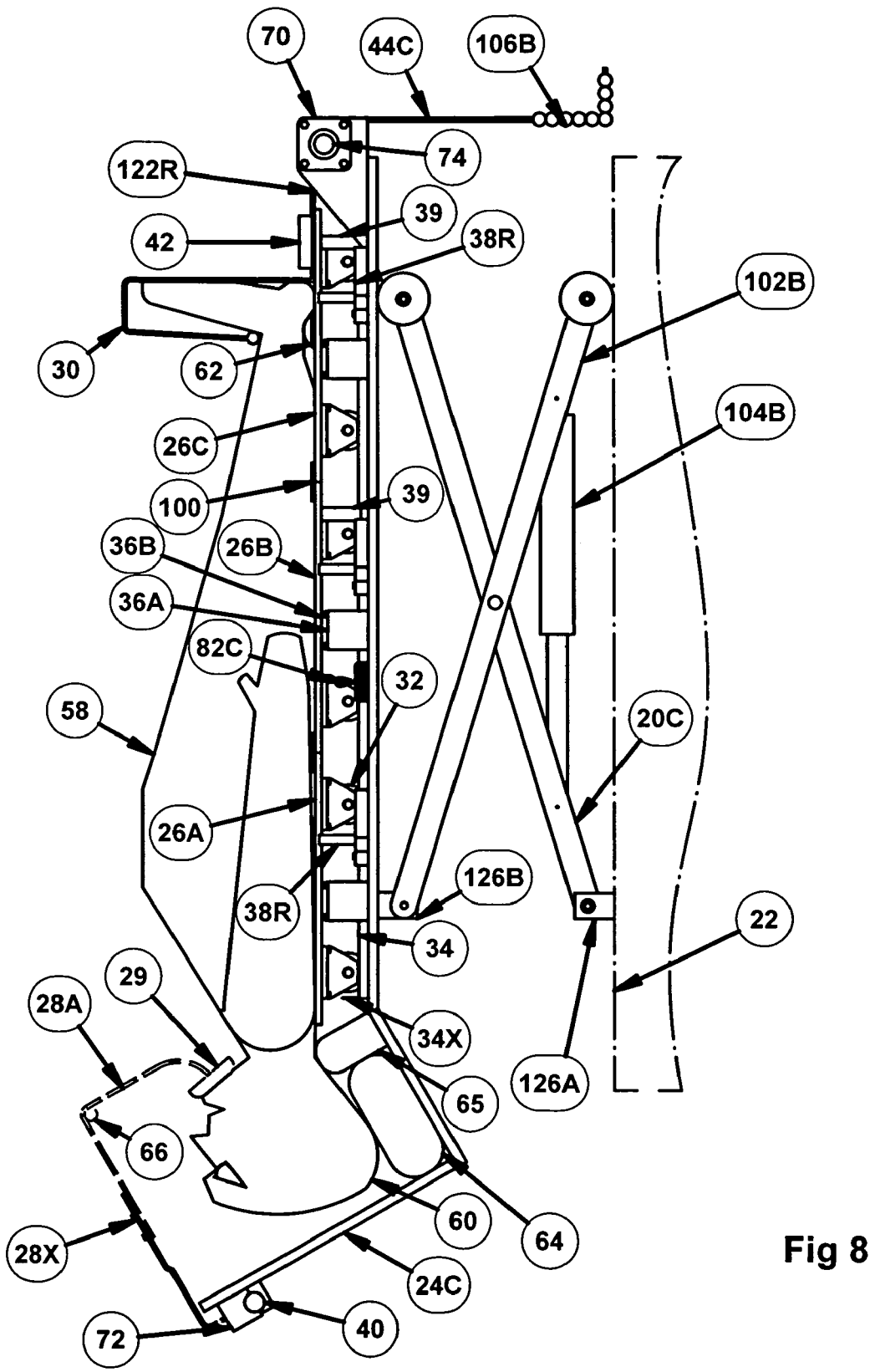

FIG. 8 Bed on bed lifting frame/bed lifted/weights suspended/traction induced

Figure 9:
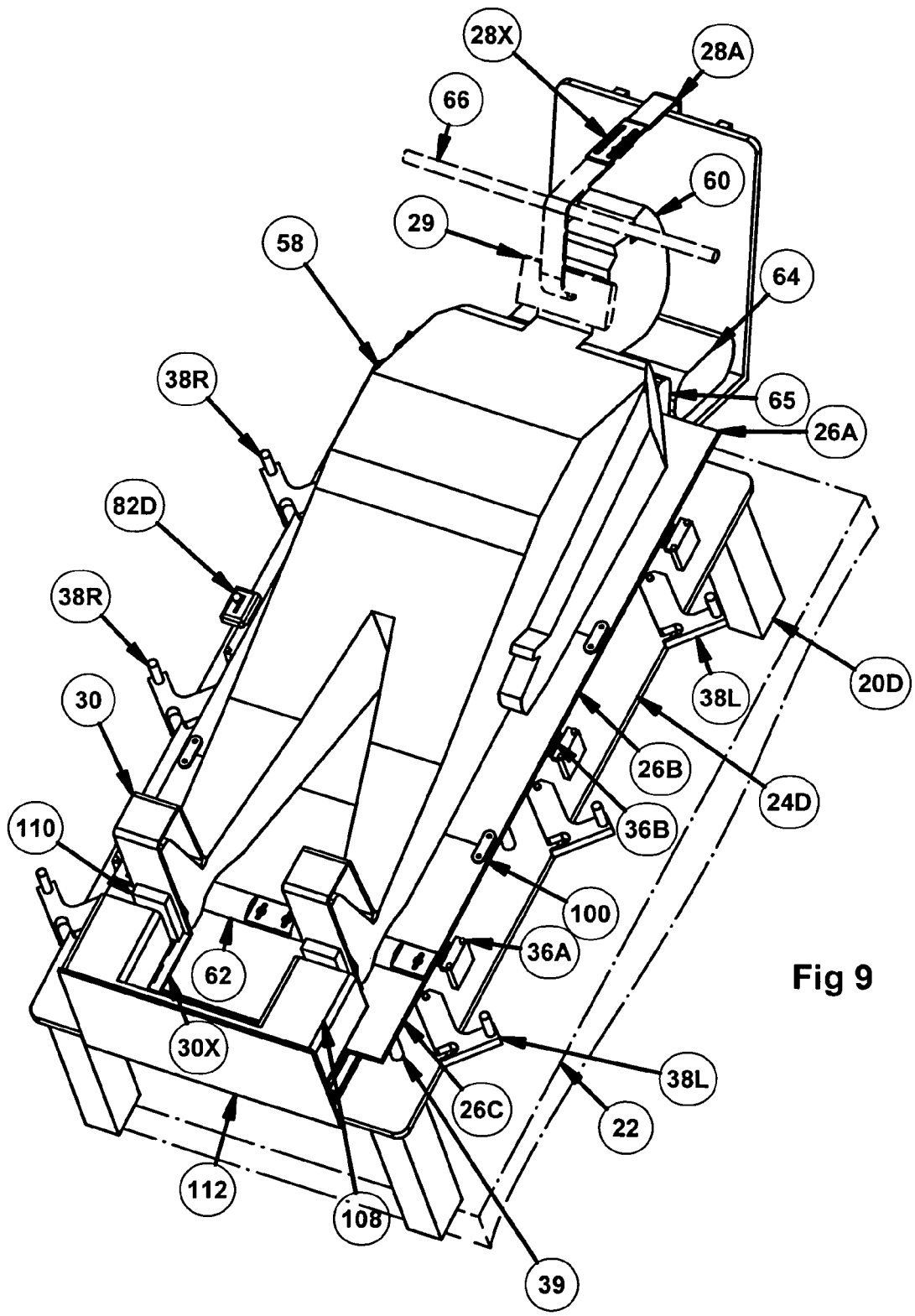

FIG. 9 Bed with electro-magnetic force generator to induce traction

Figure 10:
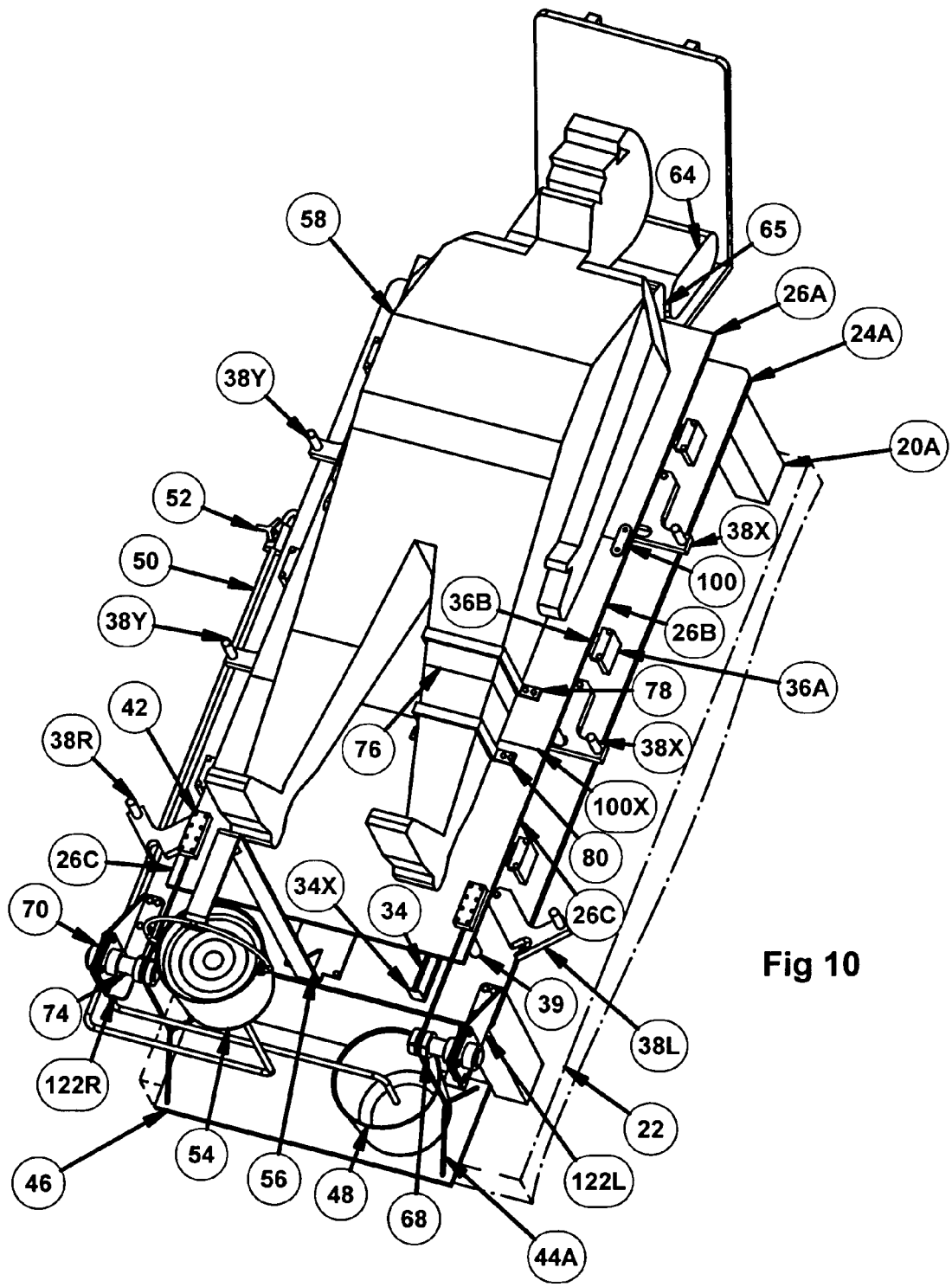
Figure 11:
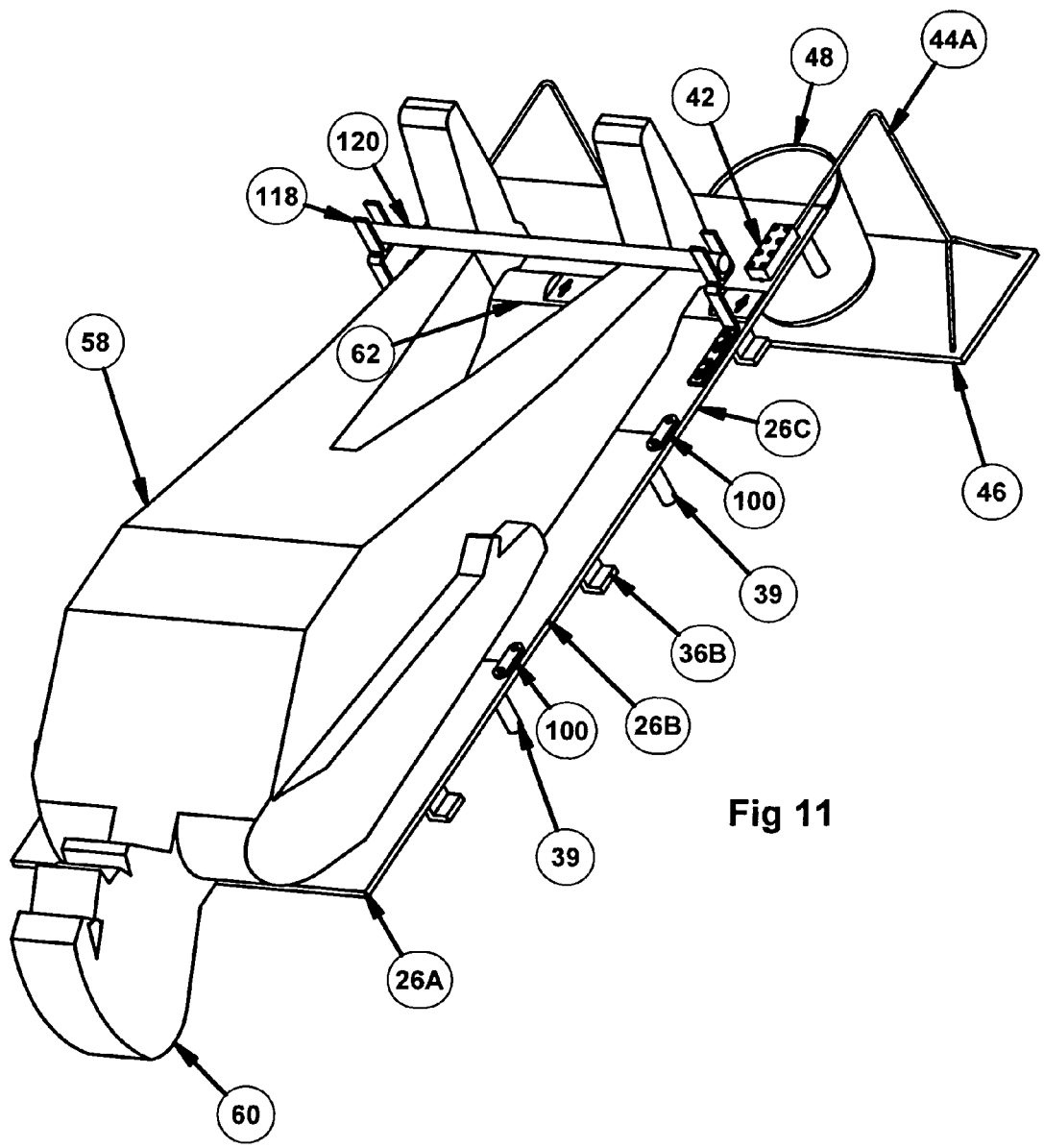
Figure 12:
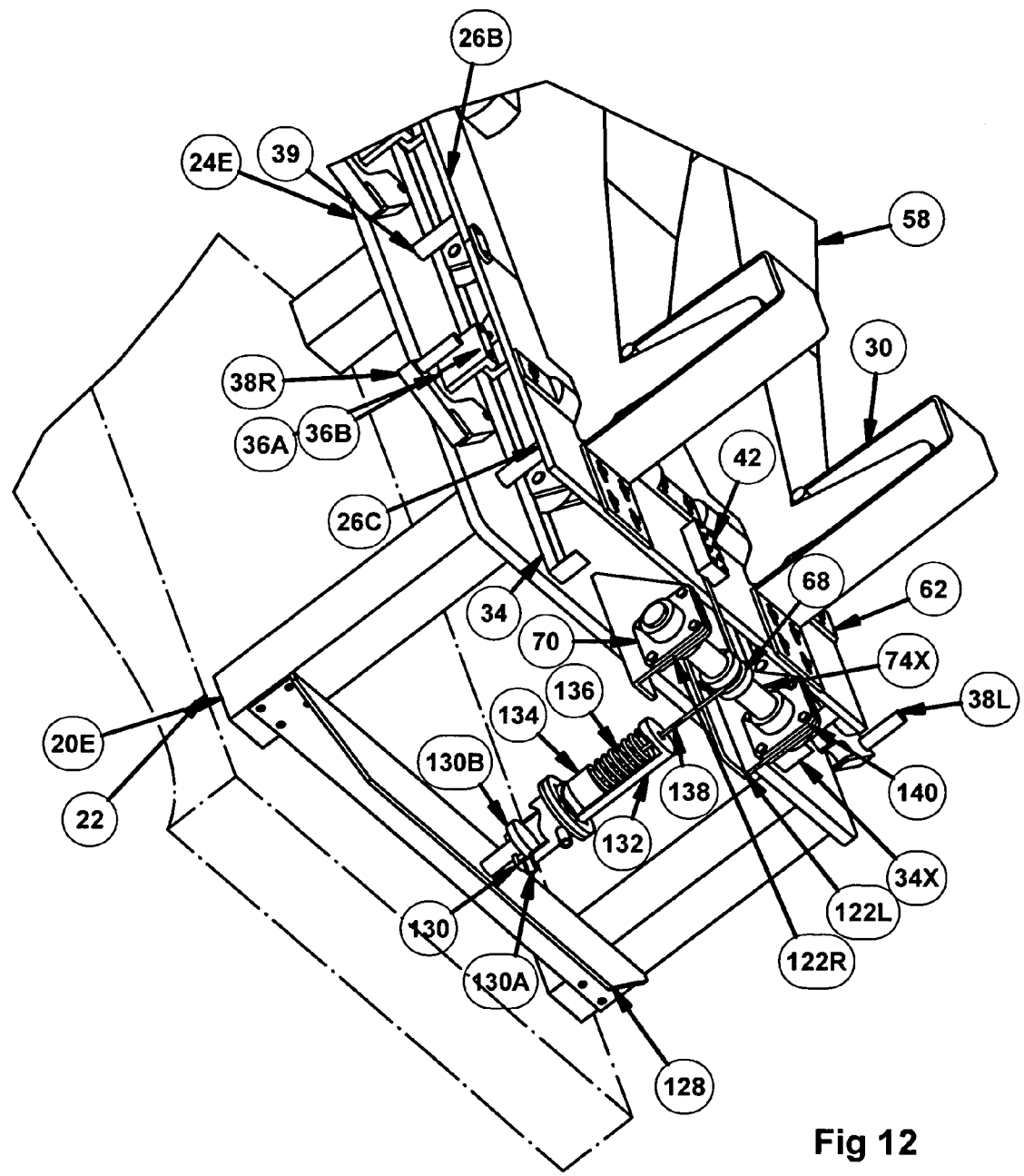
Figure 13:
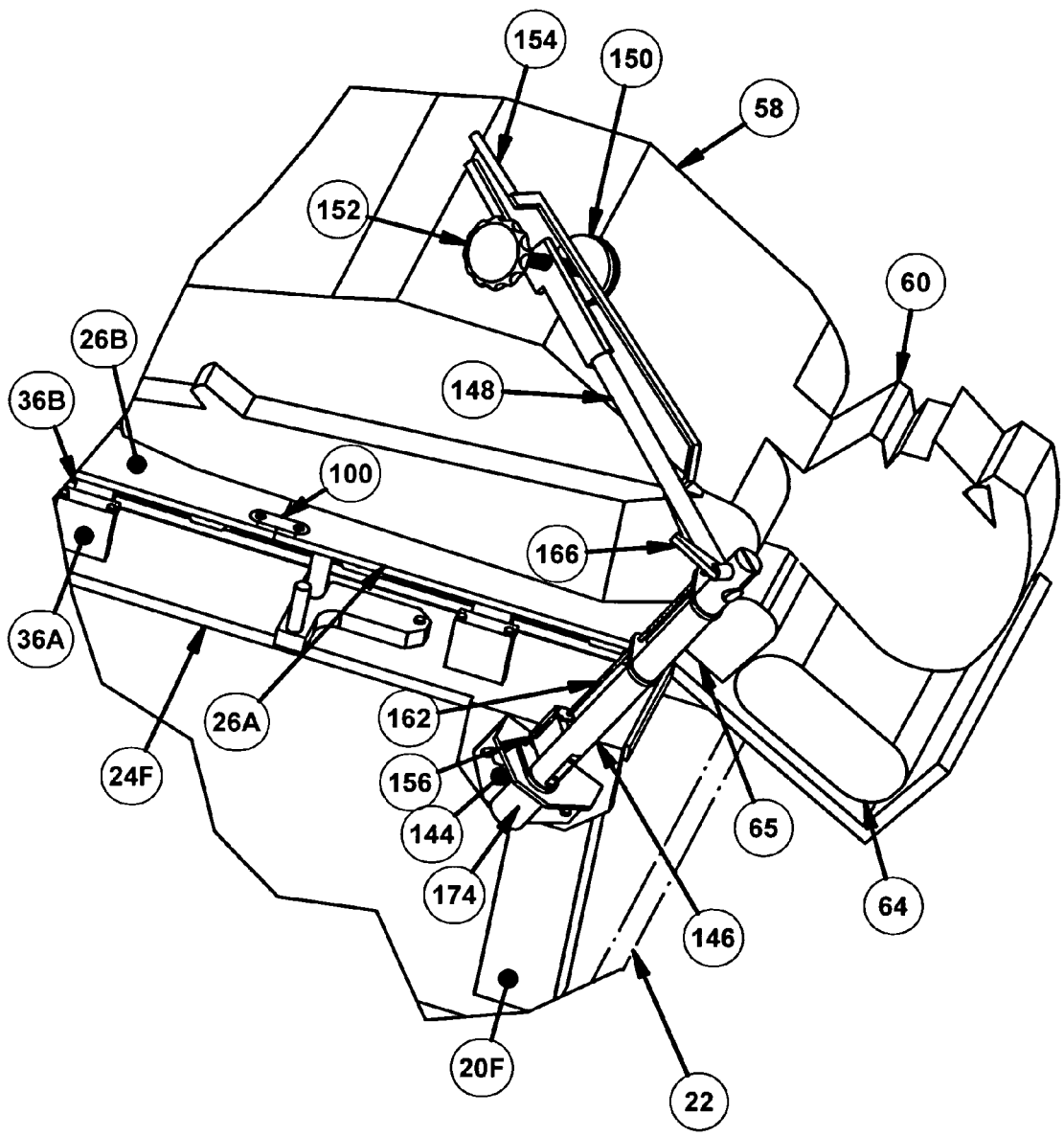
Figure 14:
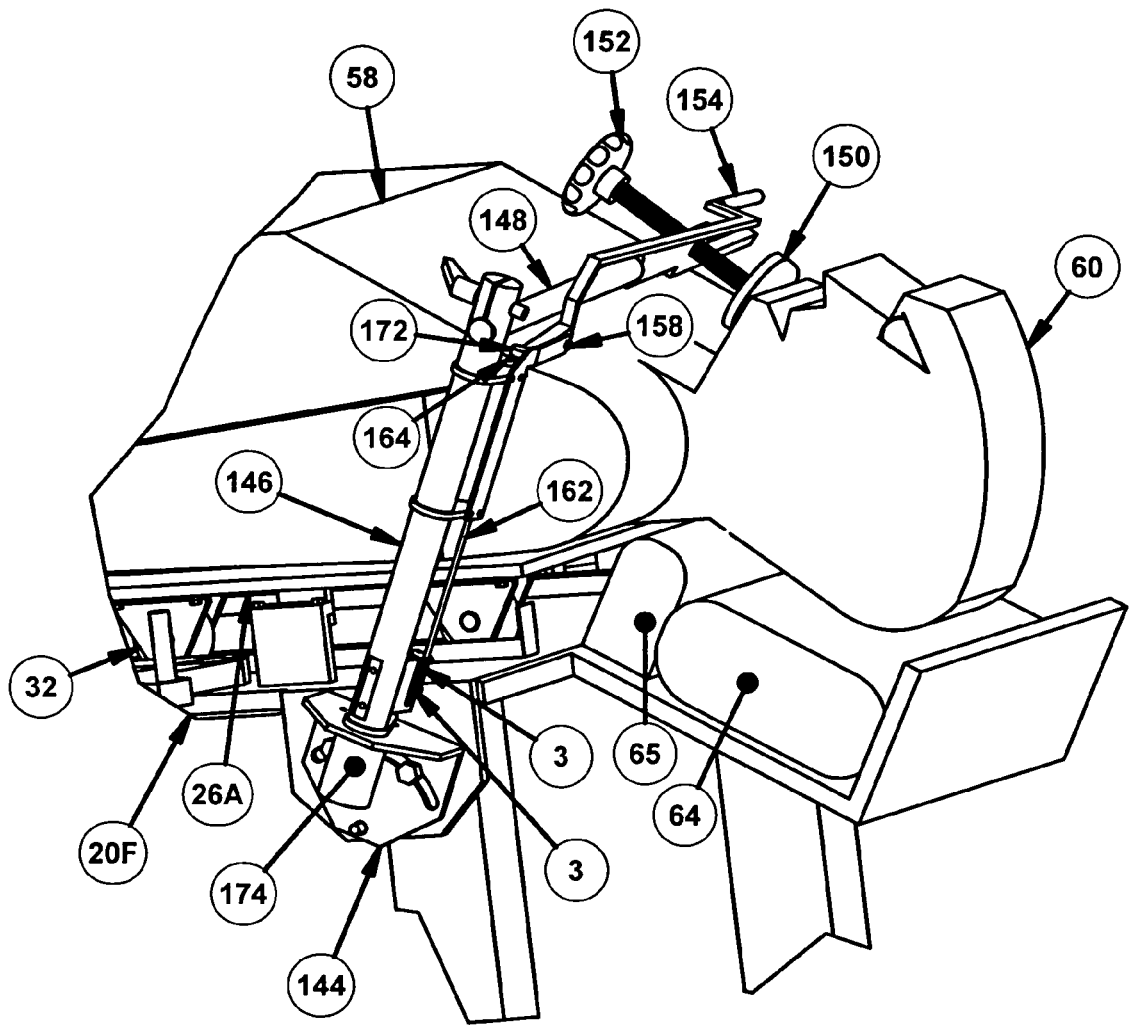
Figure 15:
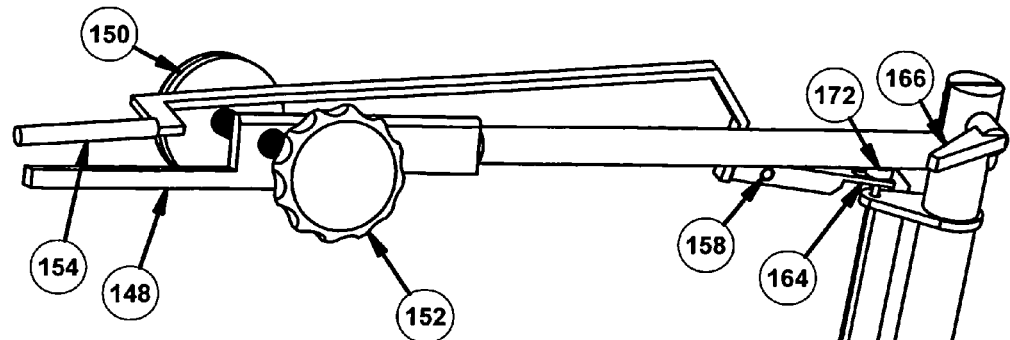
Figure 16:
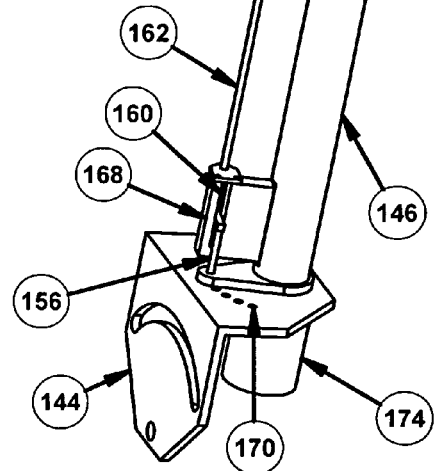
Figure 16:
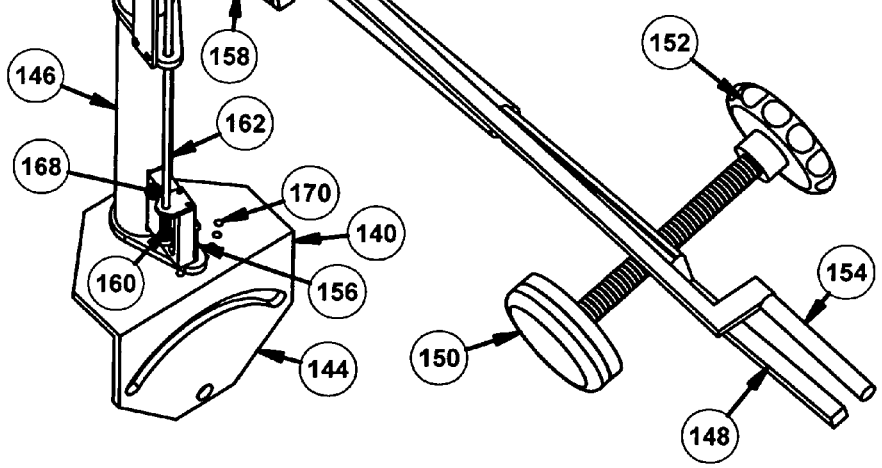
Figure 17:
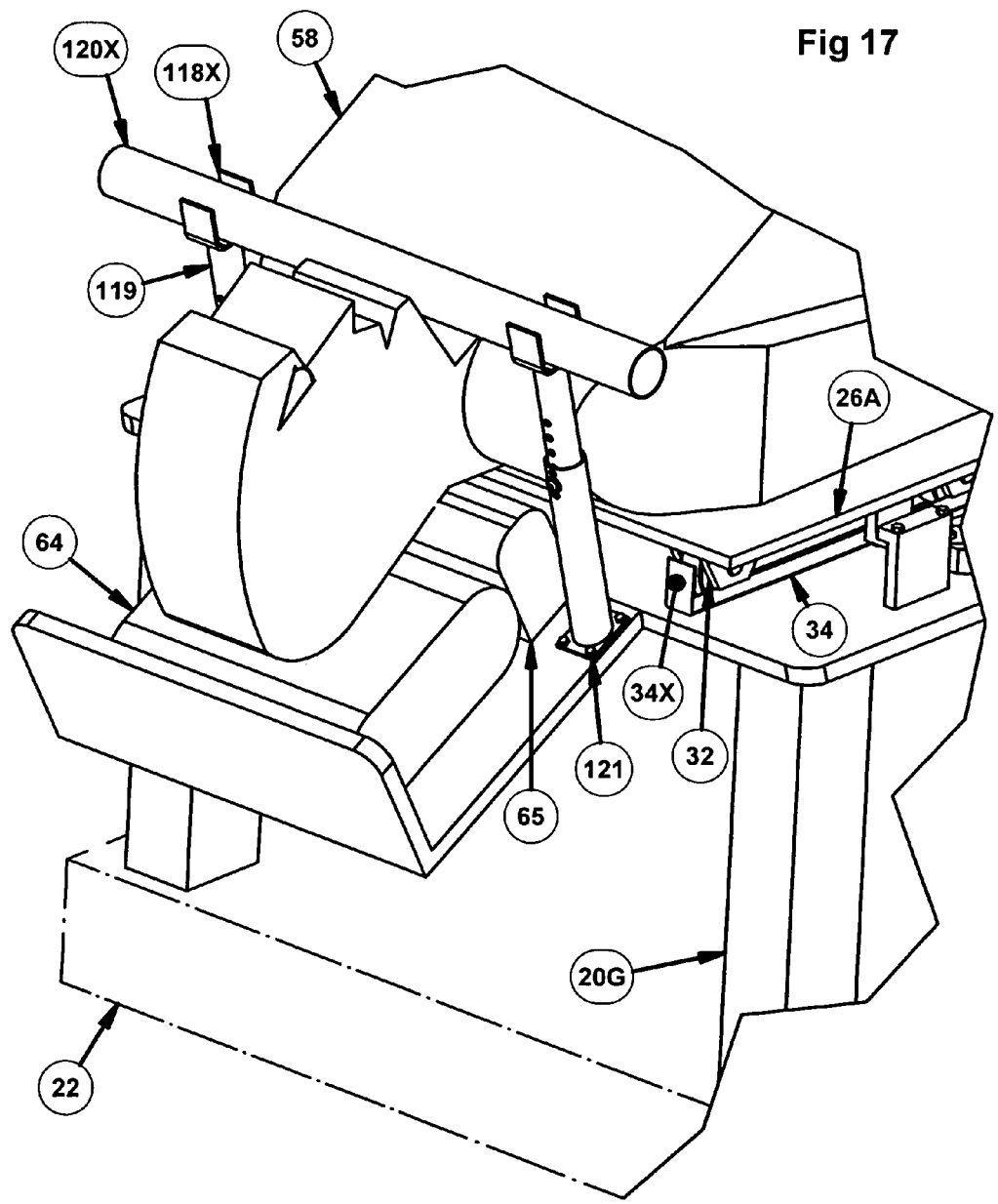
Figure 18:
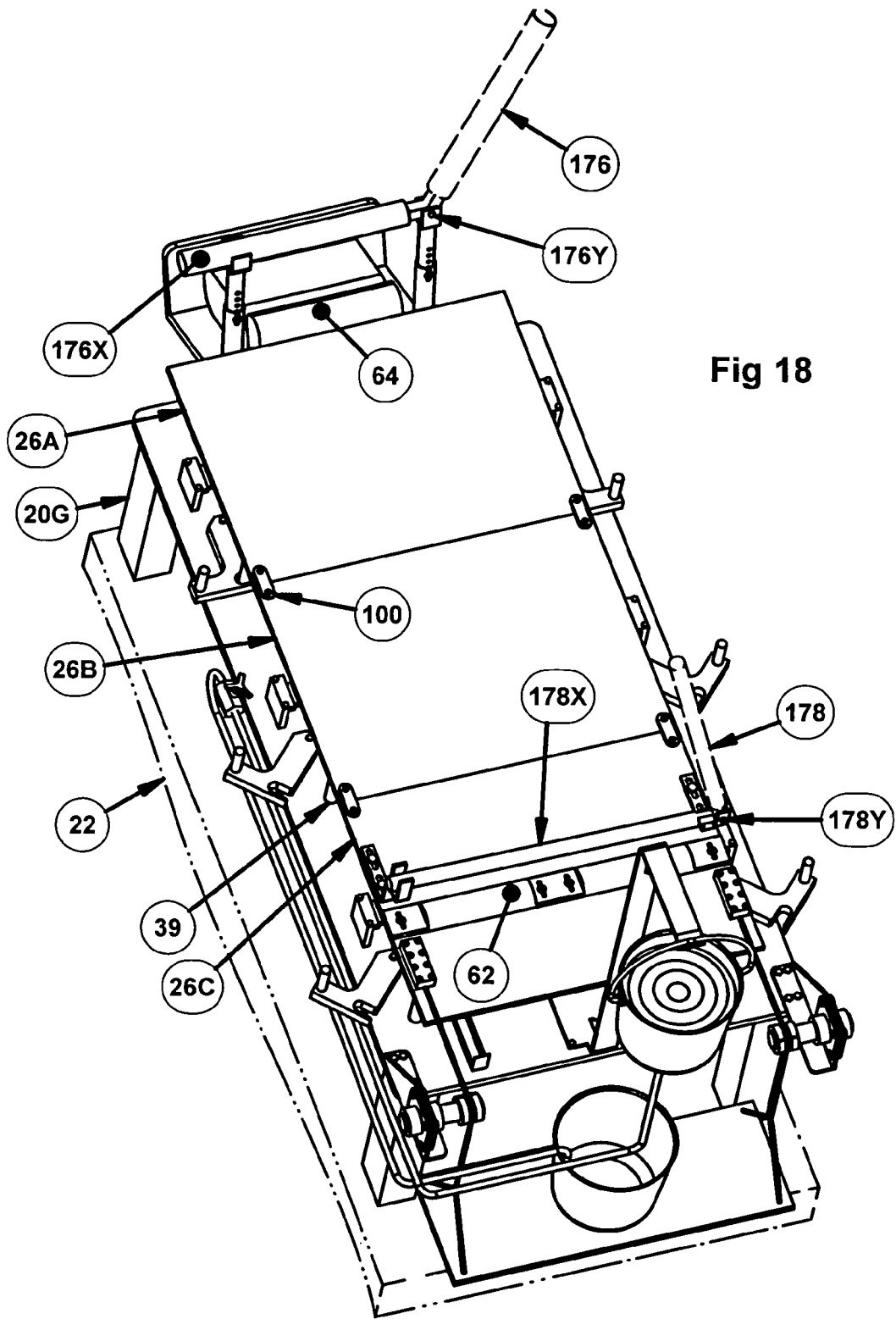

FIG. 10 Bed set up for localized traction/induced traction in a single knee joint FIG. 11 Bed's horizontally movable platform equipped with ankle restraining bar FIG. 12 Partial perspective view of bed, legs' side; use of spring to induce traction FIG. 13 Perspective view of bed with swung out chin restraint, alternate design FIG. 14 Perspective view of bed with swung in chin restraint, alternate design FIG. 15 Chin restraint mechanism assembly, $1^{st}$ alternate design, $1^{st}$ view FIG. 16 Chin restraint mechanism assembly, $1^{st}$ alternate design, $2^{nd}$ view FIG. 17 Chin restraint mechanism assembly, 2$^{nd}$ alternate design FIG. 18 Bed showing pivoted swing-away type chin and foot restraint bars

DRAWINGS, REFERENCE NUMERALS

20A Traction bed with liquid containers
20B Traction bed with weighted tray
20C Traction bed (liftable) with weights on floor
20D Traction bed with electromagnetic force traction
20E Traction bed with spring to induce traction
20F Traction bed equipped with alternate chin restraint mechanism 1$^{st}$
20G Traction bed equipped with alternate chin restraint mechanism 2$^{nd}$
22 Floor (a representation)
24A Nonmovable platform of bed 20A (bed with liquid containers)
24B Nonmovable platform of bed 20B (bed with weights in tray)
24C Vertically liftable, horizontally nonmovable platform of bed 20C
24D Nonmovable platform of bed 20D (electro magnetic force)
24E Nonmovable platform of bed 20E (spring induced traction)
24X One leg at bed's frame shown cutout to reveal hidden parts
26A Movable platform module nearest to head side of bed
26B Movable platform module in-between 26A and 26B
26C Movable platform module nearest to foot side of bed
28A Chin restraining, pivoted chin bracket; chin restraining position
28B Chin restraining, pivoted chin bracket; non restraining position
28X Adjustment area for positioning of chin restraint
29 Chin obstruction pad
30 Foot restraining bracket
30X Position adjustment flange of foot restraining bracket
32 Wheel with anti-friction bearing and bracket at movable platforms
34 Wheel guide channel
34X End stop at wheel guide channel
36A L-shaped anti-tipping bracket on nonmovable platform
36B L-shaped anti-tipping bracket on movable platform
38R Right hand, position-locking-lever, shown in unlocking position
38Y Right hand, position-locking-lever, shown in locking position
38L Left hand, position-locking-lever, shown in unlocking position
38X Left hand, -position-locking-lever, shown in locking position
39 Lock post, hanging underneath movable platform
40 Pivot shaft, for chin restraining bracket
42 Cable clamp, on movable platform module 26C
44A Cable, attached to plank-shelf, bed 20A with liquid weight for traction
44B Cable, attached to rod-weights in tray, bed 20B
44C Cable, attached to rod-weights on floor, liftable bed 20C
46 Plank-shelf, hung off of cables, bed 20A with liquid weight for traction
48 Liquid receiving container, centered on plank-shelf
50 Liquid drain tube, bed 20A
52 Liquid flow control valve
54 Liquid draining container
56 Support bracket, for fluid draining container
58 Person desirous of self induced body traction
60 Head, tilted (slight hyperextension) down to rear, looking up
62 Heel restraining bar at foot
64 Pillow-cushion, for rest of head
65 Neck support pad, near occipital bone of the head
66 Handle bar to rotate/position chin bracket
68 Shaft collars on rotatable shaft to guide cables
70 Anti-friction flange bearing, at rotatable shaft
72 Friction brake, for pivot shaft at chin bracket
74 Rotatable shaft
74X Rotatable shaft (bed 20E)
76 Left knee joint of person's leg
78 Knee strap, fixed platform side (26B)
80 Knee strap, moving platform side (26C)
82B Switch, bed 20B, to operate solenoid valve
82C Switch, bed 24C, to raise bed up and down
82D Switch, bed 24D, to operate electromagnetic apparatus
84 Fluid reservoir, bed 20B
86 Pump, to extend fluid actuator (raise tray, bed 20B)
88A Solenoid valve, in neutral position, bed 20B
88B Solenoid valve, shifted to drain fluid to lower tray, bed 20B
90 Fluid actuator to raise/lower tray, bed 20B
92 Stationary part of actuator (shown cutout), bed 20B
94 Moving part of actuator, (shown cutout), bed 20B
96 Tray, carrying traction weight-rods, bed 20B
98A Weight-rods for traction (end view), all supported in tray (no traction)
98B Weight-rods, some lifted/suspended away from tray (traction induced)
100 Strap, to connect adjacent movable platforms
100X No connecting strap between movable platforms 26B and 26C
102A Bed lift-lower mechanism, lowered position, bed 20C
102B Bed lift-lower mechanism, raised position, bed 20C
104A Linear actuator to lift-lower bed, extended to lower bed, bed 20C
104B Linear actuator to lift-lower bed, retracted to raise bed, bed 20C
106A All weights supported on floor, no traction, bed 20C
106B Some weights off of support and suspended, traction induced, bed 20C
108 Electromagnetic force generator, bed 20D
110 Bar, magnetic material, bed 20D
112 Bracket to mount electromagnetic force generator, bed 20D
118 U shaped bar bracket, at ankle restraining bar
118X U shaped receptacle, at horizontal chin restraining bar
119 Adjustable support bar, at horizontal chin restraining bar
120 Ankle restraining bar
120X Horizontal chin restraining bar
121 Fixed anchoring post, at adjustable support bar
122R Right hand bracket, at rotatable shaft
122L Left hand bracket, at rotatable shaft
124A Fluid return path to reservoir, bed 20B
124B Fluid supply path from reservoir, bed 20B
126A Lower anchor of bed's lift/lower mechanism, bed 20C
126B Upper anchor of bed's lift/lower mechanism, bed 20C
128 Angle bracket to anchor fluid actuator, bed 20E
130 Fluid actuator, bed 20E
130A Body of linear actuator (shown cutout), movable part, bed 20E
130B Piston and rod of linear actuator, nonmoving part, bed 20E
132 Spring pull cup (shown cutout), bed 20E 134 Spring rest pad, bed 20E
136 Compression spring, bed 20E
138 Traction cable, bed 20E
140 Rotatable shaft assembly, bed 20E
144 Pivot angle bracket with angular adjustment, alternate chin restraint
146 Rotatable column post, alternate chin restraint
148 Swing-cross-bar for column post, alternate chin restraint
150 Chin restraint, alternate chin restraint
152 Adjustment knob with screw, alternate chin restraint
154 Pivoted lever, alternate chin restraint
156 Lift pin to lock in position of column post, alternate chin restraint
158 Pivot, for pivoted lever, alternate chin restraint
160 compression spring, to return lift pin, alternate chin restraint
162 Lift rod, alternate chin restraint
164 Forked end at pivoted lever, to lift rod, alternate chin restraint
166 Clamp lever, to lock angular position of swing lever, alternate chin restraint
168 Slotted guide, anti-rotation for lift rod, alternate chin restraint
170 Locating holes, for lift pin positioning, alternate chin restraint
172 Lift round head at top of lift rod, alternate chin restraint
174 Pivot housing, part of angle bracket (144), alternate chin restraint
176 Swing-away chin restraint bar in swung-out position, FIG. 18
176X Swing-away chin restraint bar in restraining swung-in position, FIG. 18
176Y Pivot for swing-away chin restraining bar, FIG. 18
178 Swing-away foot restraint bar in swung-out position, FIG. 18
178X Swing-away chin restraint bar in foot swung-in position, FIG. 18
178Y Pivot for Swing-away foot restraining bar, FIG. 18

DETAILED DESCRIPTION

'General notes and explanation' for common apparatuses and methods:

The special beds (20A, 20B, 20C, 20D, 20E, 20F, 20G) each consists of five distinguishable areas;
(1) horizontally nonmovable platforms (24A, 24B, 24C, 24D, 24E, etc.),
(2) horizontally movable platforms (26A, 26B, 26C),
(3) body part restraining mechanisms at foot side (30, 62, 118, 120. etc.),
(4) restraining mechanisms at head side (28A, 28B, 65, 150, etc),
(5) traction inducing and controlling apparatuses.

Though the beds have been depicted with the head restraints on the nonmovable platform, and the foot restraints on the movable platform, the positions can be reversed and the beds redesigned. Additionally, not shown is any means to pre-tune the traction apparatus to the point of threshold of motion at zero traction with a person lying on the bed. Example: adding weights on plank-shelf (46) to a point where the wheels (32) are just about to rotate, with container (48) being empty and a person lying on the platforms, signifying a threshold of traction inducement.

In all the figures the horizontally movable platform section, on which the person (58) desirous of body traction will lie down, is shown to be made up of three modules. These are (26A) closest to head, (26C) closest to feet and (26B) in between (26A) and (26C). Optionally, the horizontally movable platform can be of a single module or any suitable number greater than one. For full body length traction all three movable platforms (26A, 26B and 26C) are conveniently connected using straps (100) so that they will behave as one platform unit, Any two adjacent platforms may be temporarily or permanently fastened to each other by straps (100), so that they behave as one. Any platform module can be temporarily or permanently locked from moving horizontally by swinging in, the swing levers (38R) and (38L) underneath it into locking position, shown as (38X) and (38Y), and by engaging posts (39) underneath movable platforms.

When one movable platform is made nonmovable by the levers, other platforms directly or serially connected to it with straps (100) are also rendered non-movable. Swing levers (38R, 38L) located on the nonmovable platform (24A, 24B, 24C, 24D, 24E) engage into corresponding lock posts (39), mounted underneath each of the movable platforms.

The horizontally non moving platforms (24A, 24B, 24C, 24D, 24E) have 'L' shaped 'anti-tipping' brackets (36A) mounted on them. These are in opposition to complementing 'L' shaped anti-tipping brackets (36B) mounted underneath the movable platforms (26A, 26B, and 26C). These opposing/complementing brackets do not come in contact with each other unless an excessive tipping condition occurs for any movable platform, say while the person (58) is climbing on to the movable platforms to place self's body. As a safety measure, such contact effectively arrests any further tipping of the movable platforms.

The wheels (32) underneath the movable platforms are guided in channels (34) to limit the motion of movable platforms horizontally into a linear path. Any excessive linear movement of the platforms in either direction is arrested by fixed stops (34X) at the ends of the channels.

To induce traction force in the entire body (embodiments $1^{st}$, $2^{nd}$, $3^{rd}$, $4^{th}$ and $6^{th}$), the person (58), first stabilizes, as needed, the movable platforms to become non-movable by swinging in, the required locking levers (38R and 38L) to be engaged (38X and 38Y) into corresponding posts (39) underneath the movable platforms. The person pre-adjusts the positions of all the necessary apparatuses, such as inverted U shaped foot-slide-in bracket (30) at (30X), heel restraining bar (62), and chin restraining bracket (28B) at (28X) or various other elements of FIGS. 13, 14, 15, 16 (148, 166, 152, etc.), FIGS. 17, 18 (119) to suit self's body. The chin will be restrained by the chin obstruction pad (29 or 150). The rear of the head will be restrained by neck support pad (65). The foot will be restrained by foot restraint bracket (30) or ankle restraining bar (120), and the heel will be restrained by heel restraining bar (62).

The following is normal generalized procedure to self induce traction:

The required swing levers (38R, 38L) are set in locking position. (38Y, 38X) The person safely climbs on to the bed, with no fear of tipping or rolling any of the movable platform (26A, 26B, 26C);—places self's feet on heel bar (62); and restrains self's feet using brackets (30) or bar (120, 178, 178X). The person then places self's head (60) on the cushion-pillow (64), with the rear top of self's neck (below the occipital bone) on the pad (65). The neck may be slightly hyper—extended with the head tilted back. This will aid in resisting the traction force at the head end.

If apparatus of FIG. 1 is provided, the person pulls down the chin restraining bracket from non-restraining position (28B) into restraining position (28A). The bracket pivots about shaft (40) against the friction brakes (72). The friction brakes are intended to keep the chin bracket steady at any pivoted angle.

If chin restraining apparatus of FIGS. 13, 14, 15, 16 is provided, then the person grasps and squeezes pivoted lever (154) against swing-cross-bar (148), thus lifting lift rod (162) to lift the lift pin (156) out of its hole (170) and setting the rotatable column post (146) free to rotate. Pivoted lever (154) pivots about the pivot (158). The fork end (164) of lever (154) pushes up the head (162X) of lift rod (162). The lift rod and lift pin (162, 156) are restricted to straight up and down motion within slotted guide (168). Compression spring (160) tends to return the lift pin (156) back into the hole in alignment (170). The column post (146) is rotated until chin restraint (150) is as close as possible to the person's chin and the lift pin (156) is aligned with a new hole (170). The squeeze is released, locking the column post (146) by trapping the lift pin (156) in a new position. Knob (152) may be turned to bring chin restraint (150) closer to and in contact with the chin.

The person now unlocks the required swing levers (38X and 38Y) setting the movable platforms free to roll. The movable platforms may have been pre-tuned with a small initial pull force, based on the person's weight, so as to immediately create a roll and take up any slack from head to feet with little or no traction induced.

The person can now self induce gradually and in controlled manner safe amounts of prescribed traction force into self's body. In all embodiments described below, the controls for traction (52, 82B, 82C, 82D), and any emergency controls are placed in close proximity to the person's hands. In discomfort or emergency the person simply pushes up on the chin restraint (66, 120X, 176X), or swings away bar (148) after squeezing the bar and lever (154). In a similar manner, the person can relieve the induced traction in a hurry, by sliding self's feet out of brackets (30) or by lifting bar (120, 178X) with feet.

Description and Operation

1st Embodiment, Preferred, FIGS. 1, 2, 3 & 4

Refer also to 'general notes and explanation' given above.

Description: The special bed 20A comprises of the non movable platform (24A). Mounted at the foot end of the non movable platform (24A) are two opposed in-line rotatable shaft assemblies, composed of brackets (122R and 122L), anti-friction bearings (70), shafts (74), and shaft collars (68). The shaft collars act as side guides for cables (44A).

Plank-shelf (46) is suspended by cables (44A) from anchoring points on movable platform (26C) using clamps (42). The liquid receiving container (48) is centrally placed on the plank-shelf (46).

Mounted centrally at the foot end of non movable platform (24A) is the bracket (56) providing a high elevation suspension for liquid supply container (54). Through tube (50) liquid from container (54) is able to find its way into receiving container (48) when the flow control valve (52) is open.

Operation: Sufficient quantity of liquid (say, water) is poured into container (54). Receiving container (48) is empty at start. The only tension in cables (44A) is minimal, solely due to the weight of the plank-shelf (46) and empty container (48) and any pre-tuning weights added at the plank to eliminate slack before inducing effective traction force. This may be considered as substantially zero or no traction force.

The person lying and restrained on the bed can gradually open flow control valve (52). Liquid begins to be transferred to receiving container (48); its weight generates tension in cables and thus induces traction force in the person's body. The flow control valve can be closed at any time when the amount of traction is felt to be sufficient.

(Not shown: if the amount of traction is found to have become excessive at any point, by the use of a pump and a different valve, the person can drain the liquid from receiving container (48), or it can be pumped back into container (54).)

Description and Operation $2^{nd}$ Embodiment, FIGS. 5 and 6

Refer also to 'general notes and explanation' given above.

Description: The special bed (20B) comprises of the non movable platform (24B). The restraints at foot and head ends shown are same as those for $1^{st}$ embodiment. Cable connections (44B) at the movable platform (26B) and cable supports at the non movable platform (24B) are similar as described for $1^{st}$ embodiment. The traction/tension inducing agents are a series of cable connected weights (98A/FIG. 5, 98B/FIG. 6) fully or partially resting in a vertically movable tray (96). One leg of the bed (20B) is shown cut away (24X) to reveal any hidden apparatus placed below the non movable platform (24B).

A fluid reservoir (84) has two fluid paths entering it. Fluid return path to reservoir is (124A), and fluid supply path to actuator (90) is (124B). Supply path (124B) goes through pump (86). Both paths go through a three position solenoid valve (88A/88B) which, depending on its actuated or default position allows fluid only to be supplied by the pump (86) to raise tray (96) with actuator's moving part (94) up, or permits fluid only to be returned to reservoir (84) from actuator (90) through its stationary part (92), or block all lines of fluid passage so that there is no fluid supply or return, and thus arresting the tray in its position.

The solenoid's position (88A/88B) is controlled by the switch (82B), which is placed in close proximity to the arm of the person's (58).

Operation: At start the actuator is fully extended; that is, the tray is fully raised. In this position, the weights (98A) being fully supported, the tension in cables being nil, the traction force is non existent.

The person on bed actuates switch (82B), shifting the solenoid to lower the tray. The solenoid is shifted to position (88B) to return fluid to reservoir (84), as required. This will leave a few weights suspended on cables (44B) since they now do not have the support of the tray. Traction is thus induced based on the number of suspended weights. To increase the traction, the tray (96) is lowered further, to suspend more weights.

To reduce the traction, or completely remove it, the switch (82A) is operated in an opposite manner to activate the pump (86) to raise the tray.

Description and Operation $3^{rd}$ Embodiment, FIGS. 7 and 8

Refer also to 'general notes and explanation' given above.

Description: Special bed (20C) comprises of the vertically movable, horizontally non movable platform (24C). The bed has no legs but rests on a scissors type lifting/lowering mechanism comprising (126A, 126B, 104A, 104B, 102A, 102B). Bed lifting and lowering is powered by linear actuator (104A, 104B)

One arm of the scissors mechanism is immovably anchored at (126A). on the floor side and the other arm is anchored to the lower platform (24C) of the bed. The switch (82C) controls the lowering and raising of the bed, and it is placed in close proximity to the arm of the person (58).

The restraints at foot and head ends shown are same as those for 1$^{st}$ embodiment. Cable connections (44C) at the movable platform (26C) and cable supports at the non movable platform (24C) are similar as described for 1$^{st}$ embodiment. The traction/tension inducing agents are a series of flexibly connected weights (106A/FIG. 7, 106B/FIG. 8) fully or partially resting on a fixed platform, say the floor (22).

When the bed is at its lowest position, all weights (106A) are on the floor (they could also be arranged to rest on any suitable fixed platform). In this position there is no tension (no-traction) in cable (44C). When the bed is lifted as needed, some weights (106B) are also raised and stay suspended. Their weight causes tension to be induced in the cables.

Operation: At start the bed is fully lowered and there is no traction induced. The switch (82C) is operated by the restrained person (58) to raise the bed as required until adequate traction is induced by the lifting of weights. To reduce traction or remove it completely, the bed is lowered as needed.

Description and Operation

4$^{th}$ Embodiment, FIG. 9

Refer also to 'general notes and explanation' given above

Description: The special bed (20D) comprises of the non movable platform (24D).

The restraints at foot and head ends shown are same as those for 1$^{st}$ embodiment. Mounted at the foot end of the non movable platform (24D) is the tension inducing apparatus consisting of an electromagnetic force generator (108), and mounting bracket (112). Switch (82D) activates and controls electrical supply to the electromagnetic mechanism (108). The generated magnetic fields induce attractive force against the magnetic bars (110), which pull the foot brackets (30) creating traction.

Operation: The person on the bed operates switch (82D) to turn on, control or turn off, the electromagnetic device.

Description and Operation

5$^{th}$ Embodiment, FIG. 10

In this embodiment traction is induced in a single knee joint (76) of the person on bed. Refer also to 'general notes and explanation' given above, but here the stated foot and head and chin restraints are not required. Also for this embodiment, straps (100) between movable platforms 26C and 26B are removed (100X).

Description: With swing levers under platforms (26A) and (26B) in swung-in position (38X and 38Y), these movable platforms (26A and 26B) have been made nonmovable. Movable platform (26C), on which the feet are resting, is the only movable platform. On the foot side of the left knee is the restraining strap (80) self fastened to movable platform (26C). On the hip side of knee is the restraining strap (78) self fastened to movable platform (26B).

Though any of the described traction inducing methods of embodiments, 1$^{st}$ through 4$^{th}$' or 6$^{th}$ may be used, in FIG. 10 liquid draining (54) and receiving (48) containers of 1$^{st}$ embodiment are shown along with other required apparatus of this embodiment. The position of fluid receiving container (48) on the plank-shelf is biased to the side of leg with knee straps (78/80). When traction is induced, only the subjected knee joint will be the beneficiary of traction force.

Operation: The operation to induce traction force is same as described for embodiment 1$^{st}$.

Description and Operation

6$^{th}$ Embodiment, FIG. 12

Refer also to 'general notes and explanation' given above.

Description: The special bed 20E comprises of the non-movable platform (24E). The traction inducing apparatus is as follows: Mounted at the foot end of the non-movable platform (24E) is a rotatable shaft assembly (140), composed of brackets (122R and 122L), anti-friction bearings (70), shaft (74X), and shaft collars (68). The shaft collars act as guides for cable (138). Clamp (42) clamps one end of the cable on movable platform (26C). The other end of the cable is attached to spring rest pad (134) housed within spring pull cap (132, shown as cut out). Compression spring (136) is trapped between rest pad (134) and inside pull cap (132), which is attached to the movable body (130A, shown with cut out) of a fluid actuator (130).

The piston/piston rod (130B) of the fluid actuator (130) is immovably connected to angle bracket (128). In turn, angle bracket (128) is fixed to the legs of bed (20E). Switch to operate to pressurize the fluid actuator (130), to extend or retract it (130A) is not shown in FIG. 12, but its placement is in close proximity to the arm of the person on bed.

Operation: At start the fluid actuator is fully extended raising pull cap (132), thus relieving any compressive force in spring (136). Hence there is no traction. When the actuator is pressurized to retract its body (130A) the spring is compressed. This pushes down on rest pad (134) and creates traction force.

The apparatus shown with a compressive spring may alternatively be redesigned to function with a tension spring, achieving a similar result for traction force.

Description and Operation

1$^{st}$ Alternate Chin Restraint, FIG. 13, 14, 15, 16

In FIGS. 13, 14 is shown partial view of bed (20F) which is provided with means to attach chin restraint apparatus. Other clarifying views are shown in FIGS. 15, 16. In FIG. 13, the apparatus is shown with chin restraint pad (150) swung out of the way of being a restraint. In FIG. 14, the apparatus is shown with chin restraint pad (150) swung in to be a restraint against induced traction force.

The circular slot and pivot hole in bracket (144) allows the chin restraint apparatus to be attached to the bed (20F) at a suitable angle based on the physique of the person on the bed.

The person on bed can adjust the angularity of the restraint pad (150) by rotating the swing-cross-bar (148). The swing-cross-bar's angular rotation within the column post can be then fixed by tightening the clamp lever (166). The position of the restraint pad (150) in relation to swing-cross-bar (148) can be adjusted by turning the adjustment knob (152). The swing-cross-bar (148) can be swung out or in and fixedly positioned as described in 'general notes and explanations'.

Description and Operation

2$^{nd}$ Alternate Chin Restraint, FIG. 17

This form of chin restraint mimics the ideas used for foot restraint with a bar, FIG. 11. The fixed anchoring posts (121), are attached to the non movable bed frame. Adjustable bars (119), adjusted so that the person's (58) chin contacts the horizontal chin restraining bar (120X), are mounted to the fixed posts (121). The person on the bed, before unlocking the (38R, 38L) movable portions of the bed places the chin restraining bar (120X) in the U shaped receptacles (118X). If the amount of traction becomes uncomfortable, or for any emergency, the person can easily reach and lift the horizontal chin restraining bar (120X) off of the U shaped receptacles (118X).

Description and Operation

3$^{rd}$ Alternate Chin (and Foot) Restraint, FIG. 18

In this embodiment the restraining bars for the chin (176), or foot (178), are straight but pivoted, and pushed out of the way of restraint before a person climbs the bed, or when the person wishes to climb out of the bed. The chin restraining bar in restraining position is shown as (176X) and similarly for the foot shown as (178X). The pivot location for chin restraining bar is (176Y) and for foot restraining bar is (178Y).

I claim:

1. A bed for a person to lie down facing up, configured for said person to facilitate self inducing of traction force in said person's body, comprising:
   (a) a plurality of nonmovable platforms configured to support a fractional portion of said person's body, and
   (b) a plurality of substantially horizontally movable platforms configured to support remainder of fractional portion of said person's body, and
   (c) means to restrain from movement, a fractional portion of said person's body, supported on said plurality of nonmovable platforms, and
   (d) means to restrain from movement said remainder of fractional portion of said person's body supported on said plurality of substantially horizontally movable platforms, and
   (e) means for said person to self induce traction force in said person's body; wherein said means to self induce traction force comprises,
   (f) a source of liquid supply, and
   (g) a container to receive liquid from said source of liquid supply, and
   (h) means to transfer liquid from said source of liquid supply to said container, and
   (i) means to control the rate and quantity of said transfer of said liquid, and
   (j) means to transmit the weight of liquid in said container as traction force in said person's body, whereby, said person may self control the rate and quantity of said self induced traction force.

* * * * *